United States Patent [19]

Heyl et al.

[11] Patent Number: 4,720,379

[45] Date of Patent: Jan. 19, 1988

[54] USE OF DIMERCAPTOPROPANESULFONIC ACID AND DIMERCAPTO-PROPANESUCCINIC ACID FOR THE PREPARATION OF PHARMACEUTICAL COMPOSITIONS AND A METHOD OF TREATMENT

[75] Inventors: Eduard Heyl; Wolfgang Parr, both of Berlin, Fed. Rep. of Germany

[73] Assignee: Hey Chem. Pharm. Fabrik GmbH & Co. KG, Fed. Rep. of Germany

[21] Appl. No.: 678,227

[22] Filed: Dec. 5, 1984

Related U.S. Application Data

[63] Continuation of Ser. No. 395,008, Jun. 30, 1982, abandoned.

[30] Foreign Application Priority Data

Mar. 25, 1981 [DE] Fed. Rep. of Germany ....... 3111770

[51] Int. Cl.$^4$ .................... A61K 45/00; A61K 31/19; A61K 31/095
[52] U.S. Cl. ..................................... 424/10; 514/557; 514/706; 514/917
[58] Field of Search .................. 424/10, 317; 514/917, 514/557

[56] References Cited

FOREIGN PATENT DOCUMENTS 2933027 2/1981 Fed. Rep. of Germany ...... 424/335

OTHER PUBLICATIONS

Cox et al., Chem. Absts., vol. 92: 140534b, 1980.
Chem. Abst., 58: 14420c, 1963.
Chem. Abst., 56: 11969f, 1962.
Chem. Abst., 60: 4435, 1964.
Chem. Abst., 78: 6783h, 1973.
Chem. Abst., 94: 203479b, 1981.
Chem. Abst., 94: 203413a, 1981.
Chem. Abst., 64: 7014h, 1969.
Chem. Abst., 78: 68811f, 1973.
Chem. Abst., 92: 190896s, 1980.
Chem. Abst., 78: 81580z, 1973.
Chem. Abst., 91: 51995q, 1979.

*Primary Examiner*—J. R. Brown
*Assistant Examiner*—John W. Rollins, Jr.
*Attorney, Agent, or Firm*—Bierman & Muserlian

[57] ABSTRACT

Use of 2,3-dimercaptopropane-1-sulfonic acid and/or 2,3-dimercaptosuccinic acid as well as their salts for combatting radiation injuries and poisonings effected by alkylating agents.

4 Claims, No Drawings

USE OF DIMERCAPTOPROPANESULFONIC ACID AND DIMERCAPTO-PROPANESUCCINIC ACID FOR THE PREPARATION OF PHARMACEUTICAL COMPOSITIONS AND A METHOD OF TREATMENT

This is a continuation of application Ser. No. 395,008, filed June 8, 1982, now abandoned.

SUMMARY OF THE INVENTION

The invention relates to the use of dimercaptopropanesulfonic acid and dimercaptosuccinic acid for the preparation of pharmaceutical compositions.

2,3-Dimercaptopropane-1-sulfonic acid and 2,3-dimercaptosuccinic acid are known compounds having the formulae:

$$H_2C-CH-CH_2-SO_3H \quad (I)$$
$$\quad | \quad |$$
$$\quad SH \quad SH$$

2,3-Dimercaptopropan-1-sulfonic acid (short name "DMPS")

$$HOOC-CH-CH-COOH \quad (II)$$
$$\quad | \quad |$$
$$\quad SH \quad SH$$

Dimercaptosuccinic acid (short name "DMSA")

The preparation of Dimercaptopropanesulfonic acid is for example known from DE-OS 2 933 027.

DETAILED DESCRIPTION OF THE INVENTION

The invention relates to the use of 2,3-Dimercaptopropane-1-sulfonic acid and/or 2,3-Ddimercaptosuccinic acid as well as their salts for combatting radiation injuries and poisonings effected by alkylating agents and for the preparation of pharmaceutical compositions.

It has now been found that DMPS and DMSA as well as their salts with a pharmaceutically acceptable base, especially their alkali metal salts, preeferably the sodium or potassium salt, are highly suitable for combatting radiation injuries and poisonings effected by alkylating agents. Thus said compounds are useful for the preparation of pharmaceutical compositions having protective activity against radiation and pharmaceutical compositions against poisonings effected by alkylating agents. Poisonings effected by alkylating agents are substantially those which are caused by alkylating agents, especially by different lost types. Examples for known lost types are the chemical warfare agents having the following formulae:

$S(CH_2CH_2Cl)_2$, $C_2H_5-N(CH_2CH_2Cl)_2$,
$CH_3-N(CH_2CH_2Cl)_2$, $N(CH_2CH_2Cl)_3$

Especially poisonings by agents of the nitrogen-lost types can be combatted effectively with the ingredients and pharmaceutical compositions according to the invention.

The active ingredients according to the invention are also very suitable for combatting radiation injuries in human and animals. Primarily they are used for combatting above-mentioned injuries in human, however, when taken as a precaution, they also exhibit a significant protective activity, especially against radiation effects.

Chemical warfare agents on the basis of lost frequently contain lewisites. Injuries caused by such mixtures also can be effectively treated using DMPS and DMSA.

DMPS and DMSA show a very low toxicity, the $LD_{50}$ value i.m. on the mouse is 1750 mg/kg for DMPS.

Usually DMPS and DMSA may be administered orally or enterally. When administered orally the therapeutical daily dosage for adults is approximately 300 to 6000 mg of active ingredient. Usually the amount of active ingredient is divided in 3 to 20 equal single doses and is administered in regular intervals.

Advantageously DMPS and DMSA is used for the preparation of pharmaceutical compositions for combatting said injuries and poisonings. Such pharmaceutical compositions contain about 100 to 200 mg of active ingredient in a capsule which is soluble in the stomach. For preparing parenteral preparations about 100 to 300 mg of active ingredient, preferably as sodium or potassium salt, are dissolved in such an amount of pyrogen-free water, that a 1 to 10% solution, especially a 5 to 10% solution, is obtained.

We claim:

1. A method of treating poisoning effected by alkylating agents of the lost type in warm-blooded animals comprising administering to said warm-blooded animals an amount of at least one compound selected from the group consisting of 2,3-dimercaptopropane-1-sulfonic acid, 2,3-dimercapto-succinic acid and their non-toxic, pharmaceutically acceptable salts sufficient to treat poisoning by alkylating agents.

2. The method of claim 1 wherein the compound is selected from the group consisting of 2,3-dimercaptopropane-1-sulfonic acid and its non-toxic, pharmaceutically acceptable salts.

3. The method of claim 1 wherein the compound is selected from the group consisting of 2,3-dimercaptosuccinic acid and its non-toxic, pharmaceutically acceptable salts.

4. The method of claim 1 wherein the alkylating agent has a formula selected from the group consisting of $S(CH_2CH_2Cl)_2$, $C_2H_5-N(CH_2CH_2Cl)_2$,
$CH_3-N(CH_2CH_2Cl)_2$ and $N(CH_2CH_2Cl)_3$.

* * * * *